(12) United States Patent
Menon et al.

(10) Patent No.: US 7,999,023 B2
(45) Date of Patent: Aug. 16, 2011

(54) PROCESS FOR MAKING PRESSURE SENSITIVE ADHESIVE HYDROGELS

(75) Inventors: Vinod P. Menon, Woodbury, MN (US); Jeffrey D. Cotton, St. Paul, MN (US); Terence D. Spawn, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 993 days.

(21) Appl. No.: 11/004,158

(22) Filed: Dec. 3, 2004

(65) Prior Publication Data

US 2006/0122298 A1 Jun. 8, 2006

(51) Int. Cl.
*C08G 73/10* (2006.01)
*C08K 5/06* (2006.01)
*C08F 220/04* (2006.01)
*C08K 5/05* (2006.01)
*C08K 5/101* (2006.01)
*C08L 31/00* (2006.01)

(52) U.S. Cl. ........ 524/376; 524/377; 524/379; 524/318; 524/386; 524/556

(58) Field of Classification Search .................. 524/376, 524/377, 379, 318, 386, 556
See application file for complete search history.

(56) References Cited

U.S. PATENT DOCUMENTS

| 3,645,835 A | 2/1972 | Hodgson |
|---|---|---|
| 3,805,769 A | 4/1974 | Sessions |
| 3,845,757 A | 11/1974 | Weyer |
| 4,233,425 A | 11/1980 | Tefertiller et al. |
| 4,310,509 A | 1/1982 | Berglund et al. |
| 4,527,087 A | 7/1985 | Taya et al. |
| 4,539,996 A | 9/1985 | Engel |
| 4,554,924 A | 11/1985 | Engel |
| 4,595,001 A | 6/1986 | Potter et al. |
| 4,640,289 A | 2/1987 | Craighead |
| 4,715,382 A | 12/1987 | Strand |
| 4,771,713 A | 9/1988 | Kinzenbaw |
| 4,771,783 A | 9/1988 | Roberts |
| 4,846,185 A | 7/1989 | Carim |
| 4,848,353 A | 7/1989 | Engel |

(Continued)

FOREIGN PATENT DOCUMENTS

DE 43 36 299 A1 11/1994

(Continued)

OTHER PUBLICATIONS

Klemchuk, P. (2005) Antioxidants: Ullmann's Encyclopedia of Industrial Chemistry—Online Edition. 22 pages. Wiley-VCH Verlag GmbH & Co. K GaA, Weinheim. [online; retrieved on Nov. 7, 2008 from the Internet <URL: http://mrw.interscience.wiley.com/emrw/9783527306732/ueic/article/a03_091/current/pdf>.].

(Continued)

*Primary Examiner* — William K Cheung
(74) *Attorney, Agent, or Firm* — Nicole J. Einerson (57) ABSTRACT

A process is provided for preparing a pressure sensitive adhesive hydrogel, comprising:
(A) providing an oligomeric precursor, the oligomeric precursor comprising a polyether moiety endcapped with ethylenic unsaturation, the oligomeric precursor being associated with methacrylic acid;
(B) providing an ethylenically unsaturated crosslinking agent selected from the group consisting of difunctional ethylenically unsaturated monomer, trifunctional ethylenically unsaturated monomer and combinations of the foregoing;
(C) free radically curing the oligomeric precursor and the ethylenically unsaturated crosslinking agent in water at a pH between about 3.5 and about 9 to provide the pressure sensitive adhesive hydrogel.

68 Claims, 2 Drawing Sheets

U.S. PATENT DOCUMENTS

| | | | |
|---|---|---|---|
| 4,849,224 A | | 7/1989 | Chang et al. |
| 4,855,294 A | | 8/1989 | Patel et al. |
| 5,012,810 A | | 5/1991 | Strand et al. |
| 5,133,356 A | | 7/1992 | Bryan et al. |
| 5,270,358 A | | 12/1993 | Asmus |
| 5,420,182 A | | 5/1995 | Chang et al. |
| 5,489,624 A | * | 2/1996 | Kantner et al. ............... 524/376 |
| 6,165,408 A | | 12/2000 | Steinmann |
| 6,746,765 B1 | * | 6/2004 | Fattman .................... 428/355 N |
| 2002/0071869 A1 | | 6/2002 | Bures et al. |
| 2003/0203011 A1 | | 10/2003 | Abuelyaman et al. |
| 2004/0167304 A1 | * | 8/2004 | Morschhauser et al. ...... 526/266 |
| 2004/0213757 A1 | * | 10/2004 | Zhu et al. .................. 424/78.19 |

FOREIGN PATENT DOCUMENTS

| | | |
|---|---|---|
| WO | WO 89/07951 | 9/1989 |
| WO | WO 02/44224 A2 * | 6/2002 |
| WO | WO 2004/003024 A1 | 1/2004 |

OTHER PUBLICATIONS

Pokorny, J.; Yanishlieva, N.; Gordon, M. (2001). Antioxidants in Food—Practical Applications. (pp. 22-70). Woodhead Publishing. [online; retrieved on Nov. 7, 2008 from the Internet <URL: http://knovel.com/web/portal/browse/display?_EXT_KNOVEL_DISPLAY_bookid=545&VerticalID=0>.].

* cited by examiner

PROCESS FOR MAKING PRESSURE SENSITIVE ADHESIVE HYDROGELS

This invention relates to a process for the manufacture of pressure sensitive adhesive hydrogel materials and to methods for the manufacture of medical articles with such pressure sensitive adhesive hydrogels.

BACKGROUND

Water swelling pressure sensitive adhesives based on polyethylene oxide (PEO) are known and are generally useful in any of a variety of articles including medical articles. The use of such materials in medical articles includes wound dressings, wound packings, contact lenses, intraocular lenses, adhesives for biological tissues, adhesion preventing materials, adsorbents for blood purification, base materials for releasing pharmacologic agents, biomedical electrodes, and the like. Materials used in dentistry may also incorporate such pressure sensitive adhesives for dental moldings or impressions, dental adhesives, restoratives, coatings, composites, sealants and the like. As used herein, "medical" applications are intended to encompass dental applications, including dental adhesives, restoratives, coatings, composites, sealants, etc. Because water swelling polymer gels have compositions and mechanical properties similar to those of biological tissues, such gels may be applied in a wide variety of fields in the future.

A common method for imparting a desired balance (tack) between cohesiveness and adhesion in pressure sensitive adhesive materials has been by the use of high-energy radiation (e.g., ultraviolet) to assist in randomly crosslinking the PEO to a predetermined cross-link density. An alternate method involves the free radical cure of a PEO-based precursor end capped with ethylenic unsaturation. This alternate method utilizes a procedure for building the molecular weight of the precursor to a desired level from low molecular weight polyethylene glycol diamines and diisocyanates through multiple condensation reactions and end capping with ethylenically unsaturated moieties. While effective, this alternate method requires precise control of the chain extension reactions which can be labor-intensive and time-consuming.

In the preparation of the foregoing precursors, PEO material of a desired molecular weight is first endcapped with reactive ethylenic unsaturation. Suitable end groups might include any of a variety of materials. Methacrylate end groups may be desired where the final adhesive material is to be used in medical applications. Methacrylates are generally easy to make and have a low potential to cause skin irritation.

It is desirable to provide adhesive materials, such as pressure sensitive adhesive hydrogels, from oligomeric precursors end capped with ethylenic unsaturation. It is also desirable to provide the foregoing adhesive materials in a more efficient and cost effective manner than has previously been provided in the art. It is desirable to provide the foregoing oligomeric precursor as a polyether moiety endcapped with ethylenic unsaturation and to further provide the foregoing adhesive hydrogels for use in medical applications, if desired.

SUMMARY

The present invention provides a process for preparing a pressure sensitive adhesive hydrogel, comprising:
 (A) providing an oligomeric precursor, the oligomeric precursor comprising a polyether moiety endcapped with ethylenic unsaturation, the oligomeric precursor being associated with methacrylic acid;
 (B) providing an ethylenically unsaturated crosslinking agent selected from the group consisting of difunctional ethylenically unsaturated monomer, trifunctional ethylenically unsaturated monomer and combinations of the foregoing;
 (C) free radically curing the oligomeric precursor and the ethylenically unsaturated crosslinking agent in water at a pH between about 3.5 and about 9 to provide the pressure sensitive adhesive hydrogel.

"Gel" or "hydrogel" means a gel material comprising a colloid, dispersion, suspension or the like in which the particles (e.g., polymer particles) are in the external or dispersion phase and water is the dispersed phase. Gels or hydrogels may exist in varying states of hydration and are typically capable of swelling, without dissolving, when contacted with water or water-based fluids (e.g., body fluids including blood, plasma, and intracellular fluid or fluids similar to body fluids such as physiological saline).

The phrase "associated with methacrylic acid" refers to the presence of methacrylic acid. In the context of the described embodiments, the methacrylic acid is typically associated with the oligomeric precursor as a by product of the reaction to provide the precursor as a polyether moiety endcapped with ethylenic unsaturation. In some embodiments, for example, polyethylene glycol is reacted with methacrylic anhydride. While methacrylic anhydride reacts to provide ethylenically unsaturated end groups on the polyether, any unreacted anhydride can be hydrolyzed to provide a residual concentration of methacrylic acid which remains associated with the oligomeric precursor. However, the foregoing phrase also encompasses methacrylic acid that has been added to the oligomeric precursor, for example.

Those skilled in the art will further understand the details of the present invention upon a review of the remainder of the disclosure including the description of the non-limiting embodiments of the invention following a brief description of the drawing.

BRIEF DESCRIPTION OF THE DRAWINGS

In describing the embodiments of the invention, reference is made to the various drawings wherein like reference numerals indicate structures and wherein.

DETAILED DESCRIPTION

The present invention provides a process for making pressure sensitive adhesive hydrogels derived from an aqueous solution of an oligomeric precursor comprising the reaction product of polyether moiety and an ethylenically unsaturated moiety. Methacrylic anhydride is used in the inventive process to provide ethylenic unsaturation on an oligomeric precursor. Any unreacted anhydride typically results in the production of methacrylic acid as a by product that can be associated with the oligomeric precursor at levels of up to a few thousand ppm. Methacrylic acid can be a significant irritant if included in an adhesive formulation for use with medical articles and the like. Moreover, the presence of methacrylic acid can hinder the free radical polymerization of the adhesive hydrogel. Removal of the acid from the reaction product has, in the past, required the use of an ultrahigh (e.g., 10 microns Hg) vacuum, thus adding significant expense to the process but still leaving at least some of the methacrylic acid associated with the oligomeric precursor. The inventive process recognizes the potentially deleterious effect of methacrylic acid on the polymerization of the oligomeric precursor to provide a pressure sensitive adhesive hydrogel. The invention provides a process that includes a curing step for curing the oligomeric precursor in the presence of methacrylic acid in water by controlling the pH of the solution during cure. The invention also provides processes for the manufacture of medical articles. The process of the invention facilitates the curing of oligomeric precursor with a crosslinker in the presence of water and residual methacrylic acid by free radical polymerization. In some embodiments, the free radical polymerization is accomplished using ultraviolet light to initiate the polymerization reaction. The hydrogel obtained by the inventive process is useful as a pressure sensitive biomedical adhesive which can be formulated to transmit/receive electrical signals when used as a component of a biomedical electrode. The adhesive hydrogel may also be used as a drug delivery device to deliver pharmaceuticals or other active ingredients to or through mammalian skin. The adhesive hydrogel may also be useful as a component in a skin covering for protecting mammalian skin or mammalian skin openings with antimicrobial agents. The invention provides a process for the manufacture of a hydrophilic, pressure sensitive adhesive hydrogel made from a water-soluble polyether derived network plasticized with an essentially non-volatile plasticizer present in an amount sufficient to form a cohesive, pressure sensitive adhesive hydrogel. The process of the invention exhibits a surprising dependence on pH during polymerization (or cure).

The hydrogel material of the present invention can be used in medical articles. In some embodiments, the gel material is absorbent, and may be advantageously transparent where inspection of an underlying material or medical condition may be desired. For medical articles such as wound dressings, transparency may permit the visual inspection of the wound without the need to first remove the wound dressing. In some embodiments, the gel material will be both absorbent and transparent.

Medical articles, particularly wound dressings, made according to the process of the invention are typically capable of removing excess exudate from the wound, maintaining a moist wound environment; allowing gas exchange so that oxygen, water vapor, and carbon dioxide can pass through the article; are thermally insulating to maintain the wound at body temperature; may be impermeable to liquids and microorganisms to minimize contamination and infection; and may be non-adherent to the wound so that no damage is done to the granulating tissue.

A hydrogel made according to the process of the present invention may be absorbent in that it is capable of absorbing fluids such as moderate to heavy amounts of various fluids (e.g., body fluids) while retaining the structural integrity and typically the transparency of the hydrogel. The hydrogel made according to the invention is "absorbent" in that it typically can absorb at least its own weight of an isotonic saline solution (0.9 wt-% sodium chloride in deionized water) after 24 hours at room temperature. That is, the material has an absorbency of at least 100 wt-%. More preferably, the gel material can absorb at least two times its weight (200 wt-% absorbency), even more preferably at least four times its weight (400 wt-% absorbency), and most preferably at least five times its weight (500 wt-% absorbency) of an isotonic saline solution after 24 hours at room temperature. Typically, gel material of the present invention can absorb up to eight times its weight of an isotonic saline solution.

In some embodiments, hydrogel materials made according to the process of the invention are relatively flexible. Flexibility allows for a medical article incorporating the hydrogel material to be easily applied to a bendable portion of a body, such as a joint, etc. Nonflexible materials may also be made according to the invention and may be used as wound packing materials, for example.

The hydrogel material made according to the process of the present invention is typically biocompatible in that the hydrogel has the ability to contact body tissues and/or body fluids without significant adverse reactions.

As mentioned, the hydrogel materials made according to the present invention possess pressure sensitive adhesive properties, and the pressure sensitive adhesive hydrogels made according to the invention typically comprise crosslinked polymers resulting from polymerization of oligomeric precursor and crosslinking agent wherein the oligomeric precursor is a polyether endcapped with ethylenic unsaturation. In some embodiments, the oligomeric precursor is a polyether methacrylate which, when reacted with a suitable crosslinking agent, provides a pressure sensitive adhesive hydrogel polymer exhibiting a glass transition temperature of less than −15° C.

In some embodiments, the pressure sensitive adhesive hydrogels made according to the present invention are bacteriostatic and possess low odor. Bacteriostatic and/or low odor properties can be inherent. In some embodiments, bacteriostatic agents and odor removing agents can be added to enhance these properties in the hydrogel material. Such materials are described in greater detail below.

The hydrogel material made according to the present invention comprises a polymer of a multifunctional poly (alkylene oxide) free-radically polymerizable oligomer (e.g., an oligomeric precursor). A multifunctional poly(alkylene oxide) free-radically polymerizable oligomer includes an alkylene oxide moiety of the formula:

wherein the mole ratio of m:n is within a range of about 1:9 to about 9:1; and $R^1$ is a (C1-C4)alkyl group, or it can be H (since polyethylene glycol is a preferred polyether). In some embodiments, the multifunctional poly(alkylene oxide) oligomer has a weight average molecular weight of at least about 6000. Oligomers with molecular weights lower than this may be undesirably brittle. In some embodiments, the multifunctional oligomer can have a weight average molecular weight of at least about 8000, and often at least about 12,000. Materials made according to the invention can have significantly higher molecular weights as well. In general, the multifunctional oligomer will have a molecular weight that provides an oligomer in a flowable and processable state at room temperature (e.g., in a liquid state). However, high molecular weight multifunctional oligomers that are not flowable at room temperature can be used if they can be processed using diluents or other additives and/or higher temperatures (e.g., extrusion temperatures). The multifunctionality of the oligomer leads to crosslinking upon polymerization. Typically, the higher the molecular weight of the multifunctional poly(alkylene oxide) oligomer, the greater the resulting distance between crosslinks in the final gel material (i.e., the lower the crosslink density). In some embodiments, a lower crosslink density will also provide desirable mechanical properties with a desirable balance of compliance (i.e., elasticity) and tensile strength as well as cohesive strength in the swollen form.

In some embodiments, pressure sensitive adhesive hydrogels made according to the process of the present invention are first prepared by exposing to a source of free radicals a difunctional polyether moiety endcapped with ethylenic unsaturation. Suitable polyether moieties may be derived from poly(ethylene glycol), for example, while ethylenic unsaturation may be provided with end groups comprising methacrylate to provide, at least in part, an oligomeric precursor comprising polyethylene glycol dimethacrylate. Other suitable polyether moieties include poly[ethylene glycol co-propylene glycol] random copolymer, for example. In embodiments where polyethylene glycol dimethacrylate is the multifunctional oligomer in the process of the invention, the oligomeric precursor may be prepared according to the process described, for example, in U.S. patent application 2003/0203011, the entire disclosure of which is incorporated herein by reference thereto. Briefly, a suitable oligomeric precursor may be obtained via the reaction of polyethylene glycol and methacrylic anhydride in the presence of antioxidant such as 2,6-ditert-butyl-4-methylphenol ("BHT") and in the absence of water or other solvent. The reaction results in a water soluble oligomeric precursor which also comprises residual methacrylic acid as a by product. At least a portion of the acid may optionally be removed from the oligomeric precursor reaction product by vacuum stripping. The water soluble multifunctional oligomer or oligomeric precursor and methacrylic acid by-product is next dissolved in water or a water based solvent to provide an oligomeric precursor solution to which additional reactants and other components may be added. Residual methacrylic acid levels in the oligomeric precursor solution may range from a few ppm to greater than about 100 ppm and up to several hundred or several thousand ppm.

A crosslinking agent can be added to the polymer precursor solution to provide a reactive solution. The crosslinking agent facilitates crosslinking during chain propagation of the polymer upon exposure to the proper conditions for cure. The crosslinking agent is water soluble and, in some embodiments, is a difunctional crosslinking agent. In some embodiments, the crosslinking agent is a trifunctional crosslinking agent. Mixtures of difunctional and trifunctional crosslinking agents can be used. Suitable difunctional crosslinking agents can include one or more of the following: polyethylene glycol di(meth)acrylate, methylene bis(meth)acrylamide, ethoxylated bisphenol A di(meth)acrylate, and alkanediol di(meth) acrylate. Suitable trifunctional crosslinking agents can include one or more of the following: ethoxylated trimethylolpropane tri(meth)acrylate, trimethylol propane tri(meth) acrylate, ethoxylated glyceryl tri(meth)acrylate, and propoxylated glyceryltri(meth)acrylate. Those skilled in the art will recognize that other crosslinking agents may be used successfully in the process of the invention.

In some embodiments, the crosslinking agent used in the process of the invention may first be dissolved in water to provide a solution of the unreacted crosslinking agent. Thereafter, the solution of crosslinking agent may be combined with the solution of oligomeric precursor to provide a reactive solution comprising the multifunctional oligomer, crosslinking agent and additional components as described herein. In some embodiments of the invention, the crosslinking agent may be dissolved in water by adding it directly to the oligomeric precursor solution without first forming a solution of the crosslinking agent to thereby provide a reactive solution. The process of the invention is not intended to be limited by the manner in which the crosslinking agent and the oligomeric precursor are mixed together to provide an aqueous reactive solution.

The amount of oligomeric precursor in the reactive solution will typically range from about 4 to 60 weight percent of the reactive solution. In some embodiments, the amount of oligomeric precursor in the reactive solution will range from about 15 to 25 weight percent of the reactive solution. The crosslinking agent is typically present at a concentration ranging from about 0.5% to about 20%.

A non-volatile polar plasticizer is typically present in the reactive solution in an amount ranging from about 96 to 20 weight percent prior to polymerization. In some embodiments, a non-volatile polar plasticizer is present in the reactive solution in an amount ranging from about 50 to 40 weight percent prior to polymerization. The plasticizer serves to minimize the crystallization of the polyether moiety of the polymeric network at ambient and mammalian body temperatures, increase the compliance of the polymeric network to give pressure sensitive adhesive properties and conformability to mammalian bodies and other curved surfaces, and modify the tack or thumb appeal of the pressure sensitive adhesive. The plasticizer can also serve as a solvent to dissolve other additives including initiators, electrolytes, and pharmacologically active components. The plasticizer is essentially non-volatile because using water alone as the plasticizer for the multifunctional oligomer will often yield materials with poor to moderate tack which are prone to rapid loss of moisture. In some embodiments, non-volatile, polar plasticizers comprise hydroxy-containing plasticizers miscible with both water and the oligomeric precursor, such plasticizers including those selected from alcohols, mixtures of alcohols, and mixtures of water and alcohols such that the mixture of alcohol, water, and oligomeric precursor is liquid in the uncured state and displays pressure sensitive tack once polymerized. Typically, the alcohol should have low volatility and should not greatly interfere with the subsequent polymerization of the oligomeric precursor.

Nonlimiting examples of suitable alcohols include glycerin, propylene glycol, dipropylene glycol, sorbitol, 1,3-butanediol, 1,4-butanediol, and trimethylol propane, for example. In some embodiments, suitable alcohols include ethylene glycol and derivatives given by Formula I:

$$MO(CH_2CH_2O)_mH \qquad I$$

wherein

M is hydrogen or $C_1$ through $C_6$ alkyl; and m is an integer ranging from about 1 to about 25.

Suitable materials for use as polar plasticizers include, for example, polyethylene glycol having a molecular weight (weight average) of 300, such as is commercially available under the trade designation "Carbowax PEG 300" from Dow Chemicals, Midland Mich. In some embodiments, the non-volatile, polar plasticizer is a mixture of 300 or 400 molecular weight (weight average) polyethylene glycol.

In applications where the final hydrogel is to be used as a conductive adhesive in a biomedical electrode, for example, the reactive solution also will comprise an ionically-conductive electrolyte. Nonlimiting examples of electrolyte include ionic salts dissolved in the adhesive to provide ionic conductivity and can include magnesium acetate, magnesium sulfate, sodium acetate, sodium chloride, lithium chloride, lithium perchlorate, sodium citrate, potassium chloride and combinations of the foregoing to enhance ionic conductivity of the pressure sensitive adhesive hydrogel. Alternatively, a redox couple such as a mixture of ferric and ferrous salts such as sulfates and gluconates can be added. The amounts of these ionic salts present in hydrogels made according to the present invention are relatively small, from about 0.5 to 10 percent by weight of the hydrogel, and preferably about 2 to 5 weight percent. When a redox couple is used, the biomedical electrode can recover from an overload potential. U.S. Pat. No. 4,846,185 (Carim) discloses a redox couple totaling not more than about 20 percent by weight of the adhesive.

In situ, solventless, polymerization or curing of the oligomeric precursor in the presence of the plasticizer is accomplished by exposing it to a source of free radicals. As one skilled in the art will recognize, free radicals may be generated by thermal, redox, or photochemical means or by exposure of the material to a source of actinic radiation. Curing of the reactive solution comprises chain propagation of the multifunctional oligomer along with or followed by reaction of the polymer chain with crosslinking agent to provide a crosslinked hydrogel.

In some embodiments, curing is accomplished by exposure of the reactive solution to conditions suitable for the generation of free radicals to initiate chain propagation of the desired polymer. When visible or ultraviolet light is used to initiate curing, suitable light sources to effect this cure include medium pressure mercury lamps and low intensity "black light" fluorescent bulbs. Suitable equipment for ultraviolet curing includes equipment such as is described in the examples herein. In the absence of an initiator in the reactive solution, exposure to actinic radiation such as electron beam irradiation or a cobalt 60 gamma source will also generate free radicals. The multifunctionality of the oligomeric precursor leads to crosslinking upon polymerization of ethylenically unsaturated moieties. Typically, the higher the molecular weight of the oligomeric precursor, the greater the distance between crosslinks (i.e., the lower the crosslink density) in the cured polymer. Such lower crosslink density typically provides hydrogels with more desirable mechanical properties. That is, the adhesive hydrogels made according to the present invention possess a balance of compliance (i.e., elasticity) and tensile strength as well as cohesive strength in the swollen form.

For free radical polymerization, a suitable initiator material is typically added to the aqueous reactive solution to initiate the polymerization reaction to form a crosslinked hydrogel according to the present invention. Typically, the initiator used in the process of the invention is one which generates a free radical upon exposure to radiation such as ultraviolet radiation. Suitable initiators include any the following: benzoin ethers, benzophenone (e.g., 4-(2-hydroxyethoxy) benzophenone and derivatives thereof), acyl phosphine oxides, acetophenone derivatives, camphorquinone, photoinitiators available under the trade designations IRGACURE and DAROCUR (Ciba Speciality Chemical Corp., Tarrytown, N.Y.) such as 1-hydroxy cyclohexyl phenyl ketone (IRGACURE 184), 2,2-dimethoxy-1,2-diphenylethan-1-one (IRGACURE 651), bis(2,4,6-trimethylbenzoyl)phenylphosphineoxide (IRGACURE 819), 1-[4-(2-hydroxyethoxy) phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173) as well as any photoinitiator with a reactive nucleophilic group. Combinations of two or more of the foregoing intiators may also be used. The initiator is generally present at a concentration of from about 0.05% to about 5% by weight of the reactive solution.

In embodiments utilizing thermal initiation, suitable thermal initiators may include azo compounds, peroxides, and persulfates and when the latter two groups are used in combination with a reducing agent such ascorbic acid or a bisulfite compound and optionally, a catalytic amount of a transition metal salt such as iron or copper, redox generation of radicals may occur even at sub-ambient temperatures.

Various other materials and additives may also be incorporated into the reactive solution for altering properties of the resulting pressure sensitive adhesive hydrogel. Nonlimiting examples include low levels of copolymerizable vinyl monomers and non-functionalized compatible polymers. Low levels of copolymerizable vinyl monomers, particularly those miscible in the oligomeric precursor/plasticizer mixture, can serve to accelerate the rate of polymerization. Preferred copolymerizable monomers include acrylic acid and methacrylic acid and their ammonium and alkali metal salts, N-vinyl pyrrolidone, acrylamide, 2-acrylamido-2-methyl propane sulfonic acid and its ammonium and alkali metal salts, hydroxylethyl acrylate, hydroxyethyl methacrylate, 2-ethoxyethyl acrylate, 2-ethoxyethyl methacrylate, and 2-(2-ethoxyethoxy)ethyl acrylate. When utilized, the amount of copolymerizable vinyl monomer preferably comprises from about 2 to about 15 weight percent of the total weight of resulting pressure sensitive adhesive hydrogel.

Addition of non-functionalized compatible polymers can enhance the viscosity of the oligomeric precursor prior to polymerization to impart better coatability for, for example, pattern coating of the resulting hydrophilic pressure sensitive adhesive hydrogel. Suitable polymers include those that are hydrophilic and compatible in the reactive solution including moderate and high molecular weight poly(ethylene oxide), poly(acrylic acid), poly(N-vinyl pyrrolidone), poly(vinyl alcohol), and poly(acrylamide). Optionally, the hydrogel material made according to the present invention can include hydrocolloids, typically in the form of particles, although they are not necessarily preferred since they can diminish the transparency of the gel material. Examples of hydrocolloids include, but are not limited to, natural gums, such as plant exudates (gum arabic, ghatti, karaya, and tragacanth), plant seed gums (guar, locust bean and acacia), seaweed extracts (agar, algin, alginate salts and carrageenin), cereal gums (starches and modified starches), fermentation or microbial gums (dextran and xanthan gum), modified celluloses (hydroxymethylcellulose, microcrystalline cellulose and carboxymethylcellulose), pectin, gelatin, casein and synthetic gums (polyvinylpyrrolidone, low methoxyl pectin, propyleneglycol alginates, carboxymethyl locust bean gum and carboxymethyl guar gum) and like water-swellable or hydratable hydrocolloids. The term hydrocolloid is used regardless of the state of hydration. The hydrogel material made according to the present invention can include an amount of the hydrocolloid such that the material is transparent (preferably, the total light transmittance is greater than 84% per ASTM D1003-00). Typically, the amount of hydrocolloid, when present, is less than about 5 wt-%, based on the total weight of the hydrogel material.

A suitable peroxide scavenger may be added to the reactive solution to scavenge peroxides formed from the oxidation of polyethylene glycol. Suitable scavengers include thiodipropionic acid and its fatty acid esters, for example.

It has surprisingly been found that controlling the pH of the reactive solution during polymerization facilitates the creation of a suitable pressure sensitive adhesive hydrogel even in the presence of the aforementioned methacrylic acid byproduct. In contrast, a failure to maintain the pH of the reactive solution in the presence of methacrylic acid will typically result in a failure of the polymerization reaction. While the art has generally recommended that methacrylate solutions be stored at an acidic pH less than 5 to prevent the hydrolysis of ester linkages, it has been discovered that the curing of the oligomeric precursor and crosslinking agent in the presence of methacrylic acid impurity is facilitated by maintaining the pH of the reactant solution within certain ranges. Adjustments to the pH of the reactive solution may be accomplished using a suitable acid, base or buffer. Prior to initiating polymerization or curing, the pH of the reactive solution may be adjusted, if necessary. The present invention comprises maintaining the reactive solution is within a desired pH range during polymerization. Typically, the pH of the reactive solution is maintained at a pH above or equal to about 3.5 and below or equal to about 9. In some embodiments, the pH of the reactive solution is maintained above or equal to about 5 and below or equal to about 9. In other embodiments, the pH of the reactive solution is maintained above or equal to about 6 and below or equal to about 8.

The pressure sensitive adhesive hydrogels made according to the present invention are useful in a variety of applications including use as high moisture vapor transmissive wound or burn dressings, as adhesives used in transdermal drug delivery, as repulpable adhesive hydrogels in, for example, splicing applications in the paper industry, and as conductive adhesive gels in biomedical electrode applications. In this last application, a high degree of pressure sensitive adhesive tack for the hydrogel may not be required when, for instance, a non-conductive, hypoallergenic pressure sensitive adhesive borders the conductive adhesive in the electrode construction.

Pressure sensitive adhesive hydrogels prepared according to the present invention possess sufficient cohesive strength to achieve generally more cohesion than adhesiveness in use, allowing for clean removal from skin. However, the adhesive hydrogels may require additional internal integrity or support in some applications such as in hydrophilic contact lenses or membranes required to withstand large pressure differentials. When used as adhesive sheets, it may be desirable to cure them with an embedded support to allow for ease in handling and dimensional stability.

Pressure sensitive adhesives hydrogels made according to the present invention can also be used in the delivery of pharmaceuticals to or through mammalian skin, such as in the form of topical or transdermal drug delivery systems. The pharmaceutical or other active ingredient can be compounded with the hydrogel adhesive after polymerization.

The pressure sensitive adhesive hydrogels made according to the present invention can also be used in therapeutic mammalian skin coverings, such as dressings, wound closure materials, tapes, and the like. For mammalian skin coverings, biologically active materials can be added to the reactive solution prior to polymerization without deleteriously affecting the biologically active material. Non-limiting examples of such other biologically active materials include broad spectrum antimicrobial agents for the reduction of bacteria levels to minimize infection risk or to treat the effects of infections at the skin or skin openings of a mammalian patient. Broad spectrum antimicrobial agents are disclosed in U.S. Pat. No. 4,310,509, the entire disclosure of which is incorporated herein by reference thereto. Nonlimiting examples of other antimicrobial agents include parachlorometaxylenol; triclosan; chlorhexidine and its salts such as chlorhexidine acetate and chlorhexidine gluconate; iodine; iodophors; poly-N-vinyl pyrrolidone-iodophors; silver oxide, silver and its salts, antibiotics (e.g., neomycin, bacitracin, and polymyxin B). Antimicrobial agents can be included in the adhesive hydrogel at concentrations ranging from about 0.01 percent to about 10 percent by weight of the total adhesive hydrogel.

Other biocompatible and/or therapeutic materials can be added to provide suitable pressure sensitive adhesive hydrogels such as compounds to buffer the pH of the final hydrogel adhesive to provide a product having a non-irritating pH suitable for use with sensitive mammalian skin tissue or to otherwise maximize antimicrobial activity. Also, penetration enhancing agents or excipients can be added to the hydrogel adhesive when the pharmaceutical or other active agent for topical or transdermal delivery so requires.

Biomedical electrodes employing pressure sensitive adhesive hydrogel made according to the process of the present invention having electrolyte contained therein are useful for diagnostic and therapeutic purposes. In its most basic form, a biomedical electrode comprises a conductive medium contacting mammalian skin and a means for electrical communication interacting between the conductive medium and electrical diagnostic, therapeutic, or electrosurgical equipment.

The pressure sensitive adhesive hydrogels made according to the process of the present invention may be included in the various articles mentioned herein by incorporating the hydrogel into the article in a suitable manner. In some embodiments, for example, the polymerized hydrogel may be laminated onto a suitable backing, release liner or other surface and thereafter, if needed, the laminated hydrogel may be cut (e.g., die cut) to an appropriate dimension. In some embodiments, the reactive solution (prior to polymerization) may be placed within the article, or a portion thereof, and thereafter be polymerized in situ so that the polymerization step in the creation of the hydrogel is also a step in the manufacture of the article. Other methods for the incorporation of pressure sensitive adhesive hydrogels into articles such as those described herein will be appreciated by those skilled in the art. Consequently, embodiments of the present invention include the step of incorporating the pressure sensitive adhesive hydrogel into an article. The aforementioned step may comprise adding the pressure sensitive adhesive hydrogel to the article or to a portion of the article by, for example, laminating and optionally die cutting the hydrogel thereafter. The aforementioned step may comprise adding the reactive solution to the article or to a portion of the article and thereafter polymerizing the reactive solution in situ to generate the hydrogel. Additionally, the aforementioned step may comprise performing the entire process of manufacturing the pressure sensitive adhesive hydrogel on or within the article or a portion thereof, including polymerizing the reactive solution in situ, to provide an article that comprises the thus manufactured hydrogel.

Figure 1:
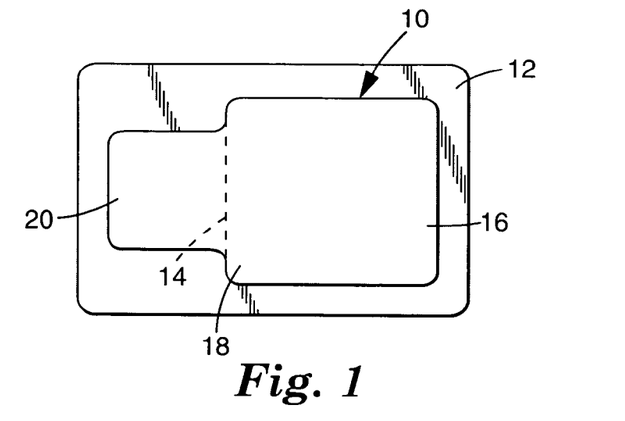
FIG. 1 is a top plan view of a biomedical electrode containing hydrophilic pressure sensitive adhesive of the present invention.
Figure 2:
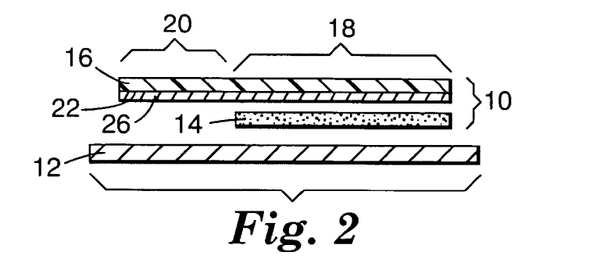
FIG. 2 is an exploded sectional view of the biomedical electrode of FIG. 1.

Referring now to the various Figures, FIGS. 1 and 2 show a biomedical electrode 10 which can be either a disposable diagnostic electrocardiogram (ECG) electrode or a transcutaneous electrical nerve stimulation (TENS) electrode. Electrode 10 is on a release liner 12 and further includes a field 14 of a biocompatible and conductive pressure sensitive adhesive hydrogel. Following polymerization, as describe herein, the pressure sensitive adhesive hydrogel is laminated onto the release liner 12 and then cut, (e.g., die cut) as needed. The field 14 of pressure sensitive adhesive hydrogel is suitable for contacting mammalian skin of a patient upon removal of protective release liner 12. The electrode 10 includes means for electrical communication 16 comprising a conductor member having a conductive interface portion 18 contacting field 14 of pressure sensitive adhesive hydrogel and a tab portion 20 extending beyond the field 14 for mechanical and electrical contact with electrical instrumentation (not shown). Means 16 for electrical communication includes a conductive layer 26 coated on at least the side 22 contacting field 14 of pressure sensitive adhesive hydrogel.

In some embodiments, ECG conductor member 16 will comprise a strip of material such as polyester film having a thickness of about 0.05-0.2 millimeters and have a coating 26 on side 22 of silver/silver chloride of about 2.5-12 micrometers, and typically about 5 micrometers thick thereon. Suitable polyester film includes that which is commercially available under the trade designation "Mellinex" 505-300, 329, or 339 film from ICI Americas of Hopewell, Va. coated with a silver/silver chloride ink commercially available under the trade designation "R-300" ink from Ercon, Inc. of Waltham, Ma. In some embodiments, a TENS conductor member 16 can be made of a nonwoven web, 20. Suitable materials for the web 20 include polyester/cellulose fibers such as those commercially available under the trade designation "Manniweb" web from Lydall, Inc. of Troy, N.Y. with a carbon ink layer 26 commercially available under the trade designation "SS24363" ink from Acheson Colloids Company of Port Huron, Mich. on side 22 thereof.

Non-limiting examples of biomedical electrodes which can use hydrophilic, pressure sensitive adhesive hydrogels made according to the present invention as conductive adhesive fields include electrodes as are disclosed in U.S. Pat. Nos. 4,527,087; 4,539,996; 4,554,924; 4,848,353 (all Engel); U.S. Pat. No. 4,846,185 (Carim); U.S. Pat. No. 4,771,713 (Roberts); U.S. Pat. No. 4,715,382 (Strand); U.S. Pat. No. 5,012,810 (Strand et al.); U.S. Pat. No. 5,133,356 (Bryan et al.) and U.S. Pat. No. 5,215,087 (Anderson et al.), the entire disclosures of which are incorporated herein by reference thereto.

Because the pressure sensitive adhesive hydrogels made according to the present invention can also be characterized as gels having pressure sensitive adhesive properties, the adhesives can also be used as the gelled contact in a conventional gel electrolyte biomedical electrode having a snap-eyelet means of electrical communication. A description of such biomedical electrodes may be found in U.S. Pat. No. 3,805,769 (Sessions); U.S. Pat. No. 3,845,757 (Weyer); and U.S. Pat. No. 4,640,289 (Craighead), the entire disclosures of which are incorporated herein by reference thereto. Nonlimiting examples of such biomedical electrodes are those marketed by a number of companies (including 3M Company under the brand "Red Dot"), including those snap-type monitoring electrodes typified by the exploded view of an electrode 50 shown in FIG. 5.

Figure 5:
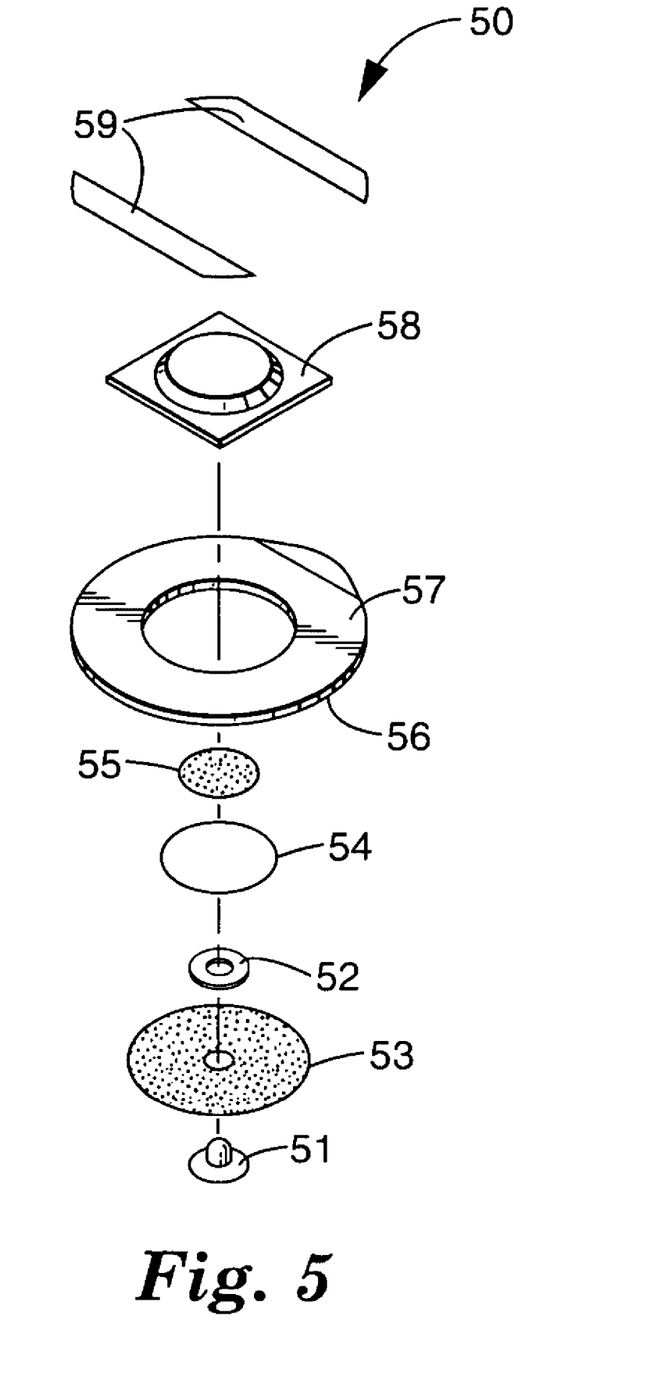
FIG. 5 is an exploded view of a biomedical electrode using the hydrophilic, pressure sensitive adhesive of the present invention.

Referring to FIG. 5, a metallic stud 51, (such as stainless steel eyelet No. 304 commercially available from companies such as Eyelets for Industry of Thomaston, Conn.) joins a plastic, metallic plated eyelet 52 (such as an ABS plastic eyelet silver-plated and chlorided commercially available from Micron Products of Fitchburg, Mass.) through an aperture in a polymeric backing 53 (such as front label stock of printed white polyethylene commercially available from Prime Graphics of West Chicago, Ill.). The inner surface of the polymeric backing is coated with an adhesive (such as a phenolic-cured smoke crepe natural rubber based adhesive). Contacting the eyelet 52 at the plated surface is a wood pulp scrim 54 (such as an "Airtex 399" scrim commercially available from James River Corporation of Green Bay, Wis.), loaded with a quantity 55 of pressure sensitive adhesive hydrogel made according to the present invention. Scrim 54 and adhesive hydrogel 55 reside in a cavity of a 0.16 cm thick coated polyethylene foam 56. A suitable means for placing the hydrogel 55 within the cavity includes placing an amount of the reactive solution within the cavity and polymerizing the solution in situ. The polyethylene foam 56 may be coated with either 12 grains of a 91:9 isooctyl acrylate:N-vinyl-2-pyrrolidone copolymer pressure sensitive adhesive or 18 grains of a 94:6 isooctyl acrylate:acrylic acid copolymer tackified with a "Foral" branded colophony acid rosin, such as "Foral AX" or "Foral 85" rosins commercially available from Hercules Corporation present in an amount of about 35-40 weight percent of the copolymer solids. The pressure sensitive adhesive is covered by a tabbed antifungal liner 57 (such as 83 pound bleached release paper under the brand "Polyslik S-8004" treated with "Calgon TK-100" brand fungicide, both liner and treatment commercially available from H. P. Smith Company of Chicago, Ill.).

Scrim 54 and adhesive 55 are protected by a cap 58, (such as a 0.25 mm "PETG" polyester film commercially available from Weiss Company of Chicago, Ill.) secured in place by dual strips 59 of adhesive tape (such as "3M" brand "Type 2185" tape). Biomedical electrodes marketed by a number of companies, and the components used in such electrodes, provide combinations of alternative materials useful as snap-type monitoring biomedical electrodes to incorporate hydrophilic pressure sensitive adhesive hydrogels made according to the present invention. Alternatively, such electrodes can be manufactured using equipment described in U.S. Pat. No. 4,640,289 (Craighead).

In some instances, the means for electrical communication can be an electrically conductive tab extending from the periphery of the biomedical electrodes such as that seen in U.S. Pat. No. 4,848,353 or can be a conductor member extending through a slit or seam in an insulating backing member, such as that seen in U.S. Pat. No. 5,012,810. Otherwise, the means for electrical communication can be an eyelet or other snap-type connector such as that disclosed in U.S. Pat. Nos. 4,640,289 and 4,846,185. Further, the means for electrical communication can be a lead wire such as that seen in U.S. Pat. No. 4,771,783. Regardless of the type of means for electrical communication employed, pressure sensitive adhesive hydrogel made according to the present invention, containing an electrolyte, can reside as a field of conductive adhesive on a biomedical electrode for diagnostic, therapeutic, or electrosurgical purposes.

Medical skin coverings employing pressure sensitive adhesive hydrogel made according to the present invention, optionally having antimicrobial and other biologically active agents contained therein, are useful for the treatment of mammalian skin or mammalian skin openings, preferably against the possibility of infection.

Figure 3:
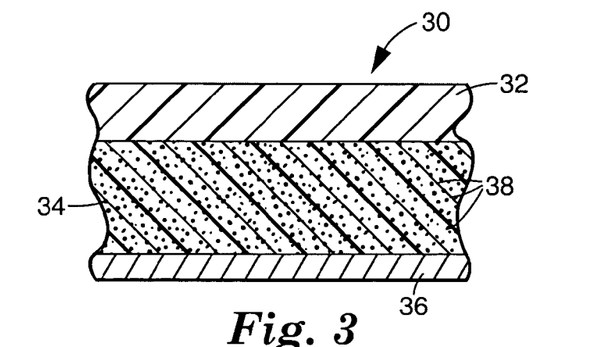
FIG. 3 is a sectional view of a medical mammalian skin covering containing hydrophilic, pressure sensitive adhesive of the present invention.

Referring to FIG. 3, a sectional view of a medical skin covering 30 is shown having a backing material 32, a layer 34 of pressure sensitive adhesive hydrogel made according to the present invention and positioned on backing material 32. The layer 34 of pressure sensitive adhesive hydrogel is protected until use by a release liner 36. Preferably, antimicrobial 38 is contained in layer 34 by adding agent 38 to the reactive solution prior to the polymerization of the material into a hydrogel. The layer 34 of pressure sensitive adhesive hydrogel may be positioned on the backing material 32 by laminating the hydrogel to the backing and optionally die cutting the hydrogel and/or the backing, as needed. In other embodiments, the hydrogel may be first laminated onto the release liner 36 before the hydrogel is positioned on the backing material 32.

For use, the release liner 36 is removed and the layer 34 of pressure sensitive adhesive hydrogel can be applied to the skin of the patient as a part of a medical tape, a wound dressing, a bandage of general medicinal utility, or other medical device having water moisture absorbing properties.

The adhesive hydrogel layer 34 may be coated on a layer of backing material 32 selected from any of several backing materials having a high moisture vapor transmission rate for use as medical tapes, dressings, bandages, and the like. Suitable backing materials include those disclosed in U.S. Pat. Nos. 3,645,835 and 4,595,001, the disclosures of which are incorporated by reference. Other examples of a variety of films commercially available as extrudable polymers include "Hytrel 4056" and "Hytrel 3548" branded polyester elastomers available from E. I. DuPont de Nemours and Company of Wilmington, Del., "Estane" branded polyurethanes available from B. F. Goodrich of Cleveland, Ohio or "Q-thane" branded polyurethanes available from K. J. Quinn & Co. of Maiden, Mass.

The layer 34 of adhesive hydrogel combined with a layer 32 of suitable backing material can be used as a dressing.

Hydrophilic pressure sensitive adhesive hydrogel made according to the present invention can be used as discrete gel particles dispersed in a continuous pressure sensitive adhesive matrix to form a two phase composite useful in medical applications, as described in co-pending, co-assigned U.S. patent application Ser. No. 07/905,490, the disclosure of which is incorporated by reference herein.

Methods of lamination and hot lamination generally involve the application of pressure, or heat and pressure, respectively, on the layer 34 of adhesive hydrogel to the backing material layer 32. The temperature for hot lamination ranges from about 50° C. to about 250° C. and the pressures applied to both lamination and hot lamination range from 0.1 Kg/cm$^2$ to about 50 Kg/cm$^2$.

Pharmaceutical delivery devices employing hydrophilic, pressure sensitive adhesives of the present invention, optionally having a topical, transdermal, or iontophoretic therapeutic agent and excipients, solvents, or penetration enhancing agents contained therein, are useful for delivery of pharmaceuticals or other active agents to or through mammalian skin.

Figure 4:
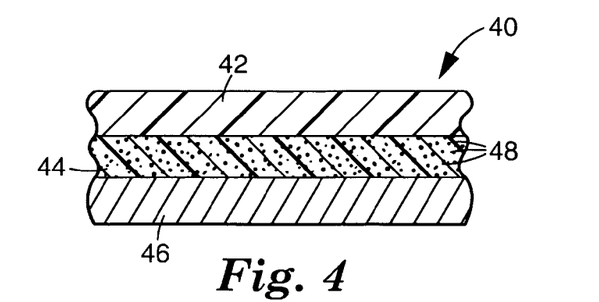
FIG. 4 is a sectional view of a pharmaceutical delivery device containing hydrophilic, pressure sensitive adhesive of the present invention.

FIG. 4 shows a sectional view of a transdermal or topical drug delivery device 40 having a backing layer 42, a layer 44 containing pressure sensitive adhesive hydrogel made according to the present invention laminated thereon and protected by a release liner 46. Other layers can be present between layer 42 and layer 44 to house pharmaceuticals or other therapeutic agents. Otherwise, as shown in FIG. 4, pharmaceutical and other agents 48 are dispersed in the adhesive hydrogel layer 44.

The backing layer 42 can be any suitable material useful for drug delivery devices. Non-limiting examples of such backing materials are polyethylene, ethylene-vinyl acetate copolymer, polyethylene-aluminum-polyethylene composites, and "ScotchPak" brand backings commercially available from 3M Company of St. Paul, Minn. (3M).

The release liner 46 can be any suitable material known to those skilled in the art. Non-limiting examples of suitable release liners commercially available include siliconized polyethylene terephthalate films commercially available from H. P. Smith Co. and fluoropolymer coated polyester films commercially available from 3M Company as "Scotch-Pak" brand release liners.

The therapeutic agent 48 can be any therapeutically active material approved for delivery topically to or transdermally or iontophoretically through the skin of a patient. Non-limiting examples of therapeutic agents useful in transdermal delivery devices are any active drug or salts of those drugs, used in topical or transdermal applications, or growth factors for use in enhancing wound healing. Other therapeutic agents identified as drugs or pharmacologically active agents are disclosed in U.S. Pat. Nos. 4,849,224 and 4,855,294, and PCT Patent Publication WO 89/07951.

Excipients or penetration enhancing agents are also known to those skilled in the art. Non-limiting examples of suitable penetration enhancing agents include ethanol, methyl laurate, oleic acid, isopropyl myristate, and glycerol monolaurate. Other penetration enhancing agents known to those skilled in-the art are disclosed in U.S. Pat. Nos. 4,849,224; and 4,855,294 and PCT Patent Publication WO 89/07951.

The drug delivery device 40 shown in FIG. 4 can be prepared using the following general method. A solution is prepared by dissolving the therapeutic agent 48 and such optional excipients as are desired in a suitable solvent and mixed into either plasticizer prior to forming the adhesive, during the formation of the adhesive, or directly into reactive solution described herein. Following polymerization, the resulting loaded adhesive hydrogel is laminated on the backing layer 42. A release liner 46 is applied to cover loaded adhesive layer 44. Die cutting is performed as needed.

EXAMPLES

The invention is further illustrated by the following non-limiting examples, in which all parts are by weight unless otherwise stated.

Test Methods

Gas Chromatographic Analysis

Residual methacrylic acid and methacrylic anhydride analysis is accomplished by an internal standard gas chromatographic test method. A mixed standard containing 0.01% (W/W) methacrylic acid and 0.001% (W/W) methacrylic anhydride was prepared in stabilized tetrahydrofuran (THF) spiked with 0.001% (W/W) internal standard of 2-ethylhexyl acrylate. The sample was dissolved and diluted to 10% (W/W) in stabilized THF spiked with 0.001% (W/W) 2-ethylhexyl acrylate internal standard. Separation was accomplished using an Rtx-1701, 30 m, 0.32 mm ID, 0.5 μm df capillary GC column (14% cyano-propyl-phenyl-86% dimethyl polysiloxane). Helium was used as the carrier gas. The following column flow program was used: 3.6 mL/min for 15 minutes then ramp at 3 mL/min for 2 minutes to a final flow of 9.6 mL/min and hold for 1 minute. The following oven temperature program is used: 50° C. for 0 minutes then ramp at 10° C./min to 200° C. holding for 0 minutes then ramp at 30° C./min to 270° C. and hold for 0.67 minute. The gas chromatograph is operated in splitless injection mode with the purge valve off initially and then on at 1 minute. The injection port is operated at 170° C., and the flame ionization detector (FID) was maintained at 290° C. An injection volume of 3 μL for the standard and sample was utilized.

Tack Value

The adhesive composition was evaluated for initial tack immediately following curing. In this test, firm pressure was applied to the sample with a thumb and the thumb was removed. Tack was qualitatively assessed and assigned a value of 1 through 6 according to Table 1. On this scale, tack values of 2, 3, and 4 represented adhesives with a desirable balance of sufficient compliance to possess tack and sufficient integrity to possess cohesive strength. However, unacceptable values are 1, 5 and 6. These values represent: (1) compositions which have essentially no tackiness, (5), which lack cohesive strength and exhibit adhesive transfer and (6) an uncured composition, retaining its liquid form after the cure cycle.

TABLE 1

| Tack Value | Cohesive Quality | Adhesive Quality |
|---|---|---|
| 1 (no tack) | Highly Cohesive | Non-adhesive |
| 2 (acceptable tack) | Moderately Cohesive | Weakly Adhesive |
| 3 (best tack) | Moderately Cohesive | Moderately Adhesive |
| 4 (acceptable tack) | Moderately Cohesive | Highly Adhesive |
| 5 (residue transfer) | Weakly Cohesive | Highly Adhesive |
| 6 (uncured) | Non-Cohesive | Highly Adhesive |

Example 1A

In general, polyethylene glycol with a nominal molecular weight of 12000 was endcapped with methacrylate to provide polyethylene glycol dimethacrylate ("DMPEG") as an oligomeric precursor using the procedure set forth in U.S. Patent application 20030203011. Specifically, 500 grams of Polyglykol 12000 S (0.0365 moles, obtained from Clariant GmbH, Gendorf Germany) was melted under an atmosphere of dry nitrogen at 100° C. To the melted material was added 0.23 grams of 2,6-di-tert-butyl-4-methylphenol ("BHT" obtained from Aldrich Chemicals of Milwaukee, Wis.) and 14.08 grams of methacrylic anhydride (0.091 moles, obtained from Aldrich Chemicals of Milwaukee, Wis.). The resulting mixture was held at 100° C. under an atmosphere of dry air for 6 hours, and then cooled to 65° C. The resulting material was then vacuum stripped to remove most of the excess methacrylic anhydride and the byproduct methacrylic acid using a 0.04 $m^2$ glass rolled film evaporator with an internal condenser. The jacket was set at 100° C., the condenser at 15° C., the rotor at 175 rpm, and the vacuum at approximately 6 microns Hg.

The completion of the reaction was determined by monitoring the unreacted —OH functionality of PEG used in the reaction. The residual —OH groups are derivatized with phenylisocyanate. The derivative was separated by HPLC, using on a size exclusion column (Jordi 100A) and determined by measuring its UV absorption at 230 nm. The analysis showed that the capping reaction was 97% complete. The residual methacrylic anhydride and methacrylic acid levels of the DMPEG were determined by GC to be 122 ppm and 1904 ppm respectively.

10 grams of the DMPEG was dissolved in 45 grams of DI water. To this solution was added 4 grams of potassium chloride (obtained from Aldrich Chemicals of Milwaukee, Wis.), 35 grams of polyethylene glycol 300 (obtained from Dow Chemicals of Midland, Mich.), 1.7 grams of ethoxylated trimethylolpropane triacrylate (crosslinking agent) (obtained from Sartomer Chemicals of Westchester, Pa., under the brand SR 415), and 0.2 grams of 2-hydroxy-1-[4-(hydroxyethoxy)phenyl]-2-methyl-1-propanone (available from Ciba-Geigy Corporation of Hawthorne, N.Y., under the brand IRGACURE 2959). The pH of the reactive solution was measured at 5.0. The reactive solution was UV cured in polyethylene foam wells that were 1.5 mm (60 mils) deep using a Fusion 300 system from Fusion UV Inc., equipped with a 118 W/cm (300 W/inch) H bulb. The total energy was maintained at 550 mJ/$cm^2$.

Examples 1B and Comparative Example A

Two additional lots of reactive solution were made as in Example 1A, except Comparative Example A was adjusted to a pH of 3.5 with acetic acid and Example 1B was pH adjusted to 7.5 with sodium hydroxide (acetic acid and sodium hydroxide were both obtained from Aldrich Chemicals of Milwaukee, Wis.). Comparative Example A and Example 1B were also UV cured in wells under the Fusion 300 System UV lamp. The tack values and residual methacrylic acid levels are shown in Table 2.

TABLE 2

| Example Number | pH of formulation | Methacrylic acid (ppm) | Tack Value |
|---|---|---|---|
| 1A | 5.0 | 95.2 | 4 |
| Comparative Ex. A | 3.5 | 95.2 | 5 |
| 1B | 7.5 | 95.2 | 3 |

Comparative Examples B-E and Examples 2A-2D

Reactive solution was formulated as in Example 1A. Comparative Examples B-E were made from the reactive solution and the methacrylic acid concentrations were adjusted by the addition of neat methacrylic acid (obtained from Aldrich Chemicals of Milwaukee, Wis.) so that the acid concentrations were 225, 350, 600, and 850 ppm, respectively. The pH values were measured after the addition of neat methacrylic acid and the formulations were subjected to conditions for curing as in Example 1A. After noting that Comparative Examples B-E failed to cure and assigning tack values, the uncured reactive solutions of Comparative Examples B-E were then pH adjusted with sodium hydroxide to a neutral pH and were again subject to cure conditions. The resulting hydrogel materials were designated as Examples 2A-2D. Tack values for Examples 2A-2D and for Comparative Examples B-E are shown in Table 3.

TABLE 3

| Example Number | pH of formulation | Methacrylic acid (ppm) | Tack |
|---|---|---|---|
| Comparative Ex. B | 4.7 | 225 | 6 |
| Comparative Ex. C | 3.7 | 350 | 6 |
| Comparative Ex. D | 3.5 | 600 | 6 |
| Comparative Ex. E | 3.2 | 850 | 6 |
| 2A - Neutral pH | 7 | 225 | 3 |
| 2B - Neutral pH | 6.6 | 350 | 3 |
| 2C - Neutral pH | 7.2 | 600 | 3 |
| 2D - Neutral pH | 7.6 | 850 | 3 |

Example 3A-3H

A reactive solution was formulated identically to the procedure outlined in Example 1A. Examples 3A-3D were made from the precursor and the acid concentrations were adjusted by the addition of neat acrylic acid (obtained from Aldrich Chemicals of Milwaukee, Wis.). The acrylic acid concentrations were adjusted to 125, 250, 500, and 750 ppm in Examples 3A-3D, respectively while the level of methacrylic acid was maintained at 95 ppm. The pH values were measured after the addition and the formulations were cured as in Example 1A. Four additional reactive solutions, Examples 3E-3H were prepared in an identical manner except that the reactive solutions of 3E-3H were then pH adjusted with sodium hydroxide to neutral pH and cured. The tack values for Examples 3A-3H are in Table 4.

TABLE 4

| Example No. | pH | Acrylic acid (ppm) | Methacrylic acid (ppm) | Tack |
|---|---|---|---|---|
| 3A - Low pH | 4.4 | 125 | 95 | 4 |
| 3B - Low pH | 4.3 | 250 | 95 | 4 |
| 3C - Low pH | 4.0 | 500 | 95 | 4 |
| 3D - Low pH | 3.5 | 750 | 95 | 4 |
| 3E - Neutral pH | 6.7 | 125 | 95 | 3 |
| 3F - Neutral pH | 6.5 | 250 | 95 | 3 |
| 3G - Neutral pH | 7.7 | 500 | 95 | 3 |
| 3H - Neutral pH | 6.4 | 750 | 95 | 3 |

Examples 3I and 3J and Comparative Examples F and G

A reactive solution was formulated identically to the procedure outlined in Example 1A. Comparative Examples F and G were made from the precursor and the acid concentrations were adjusted by the addition of neat acrylic acid (obtained from Aldrich Chemicals of Milwaukee, Wis.). The acrylic acid concentrations were adjusted to 750 ppm in Comparative Example F and to 2500 ppm in Comparative Example G while the level of methacrylic acid was adjusted to 300 ppm in both Comparative Examples F and G. The pH values were measured after the addition and the formulations were cured as in Example 1A. Two additional reactive solutions, Examples 3I and 3J were prepared in an identical manner with Example 3I having an acrylic acid content of 750 ppm and Example J having an acrylic acid content of 2500 ppm. The level of methacrylic acid was adjusted to 300 ppm in both Examples 3I and 3J. The reactive solutions of 3I and 3J were pH adjusted with sodium hydroxide to neutral pH and cured. The tack values for Comparative Examples F and G and Examples 3I and 3J are set forth in Table 5.

TABLE 5

| Example No. | pH | Acrylic acid (ppm) | Methacrylic acid (ppm) | Tack |
|---|---|---|---|---|
| C. Ex. F | 3.4 | 750 | 300 | 5 |
| C. Ex. G | 3.2 | 2500 | 300 | 5 |
| 3I | 7.1 | 750 | 300 | 3 |
| 3J | 7.5 | 2500 | 300 | 3 |

Example 4 and Comparative Example H

Example 4 was prepared in the following manner. In general, a water-soluble random copolymer of ethylene glycol and propylene glycol (75/25) at a nominal molecular weight of 16000 was obtained from Dow Chemical Company and capped with methacrylic anhydride as described in US Patent application 2003/0203011. Specifically, 480 grams of UCON-75H-90000 (0.030 moles, obtained from Dow Chemical Co. of Midland, Mich.) 0.25 grams of 2,6-di-tert-butyl-4-methylphenol (BHT obtained from Aldrich Chemicals of Milwaukee, Wis.), 16.3 grams (0.106 moles) of methacrylic anhydride (obtained from Aldrich Chemicals of Milwaukee, Wis.) and 2 grams (0.023 moles) of methacrylic acid (obtained from Aldrich Chemicals, of Milwaukee, Wis.) were combined and heated under an atmosphere of 90/10 nitrogen/oxygen for a total of 48 hours. During this time, every 12 hours an additional 0.12 grams of BHT was added. At the end of the reaction, approximately 5 mm Hg of vacuum was pulled on the reaction vessel, and air was purged into the mixture for 1 hour to sweep out most of the unreacted methacrylic anhydride. Finally, 1 gram of water was added, and the mixture was stirred at 65° C. for 3 hours.

The residual methacrylic acid was determined to be 1.4% w/w of the polyglycol dimethacrylate. The polyglycol dimethacrylate was formulated into an oligomeric precursor solution by dissolving 10 grams in 45 grams of DI water. To this solution was added 4 grams of potassium chloride (obtained from Aldrich Chemicals of Milwaukee, Wis.) 26 grams of methoxypolyethylene glycol 350 (obtained from Dow Chemicals of Midland, Mich.), 10 grams of propylene glycol (Aldrich Chemicals, Milwaukee, Wis.), 4 grams of ethoxylated trimethylolpropane triacrylate (obtained from Sartomer Chemicals of Westchester, Pa., under the brand SR 415), and 0.2 grams of 2-hydroxy-1-[4-(hydroxyethoxy)phenyl]-2-methyl-1-propanone (available from Ciba-Geigy Corporation of Hawthorne, N.Y., under the brand IRGACURE 2959). The pH of the solution was adjusted to 7.0 with sodium hydroxide. Example 4 was then UV cured in polyethylene foam wells that were 1.5 mm (60 mils) deep using a Fusion 300 system from Fusion UV Inc. equipped with a 118 W/cm (300 W/inch) H bulb. The total energy was maintained at 550 mJ/cm$^2$. An identical precursor solution, Comparative Example H, was prepared in the same manner as Example 4, except its pH was adjusted to 3.5 with acetic acid. Comparative Example H was also exposed to the same curing conditions as Example 4, but Comparative Example H failed to cure. The tack values for Example 4 and Comparative Example H are shown in Table 6.

TABLE 6

| Example Number | pH of formulation | Methacrylic acid (ppm) | Tack |
|---|---|---|---|
| 4 | 7 | 1400 | 3 |
| Comparative Ex. H | 3.5 | 1400 | 6 |

Examples 5A, 5B and Comparative Examples I, J

In general, an oligomeric precursor solution containing polyether diacrylamide was synthesized according to the procedure outlined in U.S. Pat. No. 5,489,624 assigned to Kantner et al. Specifically, an amount of 2,000 MW poly(ethylene oxide)diamine (available from Texaco Chemical Company of Houston, Tex., under the brand "Jeffamine ED-2001") was melted by holding in a 55° C. oven for 4 hours. An amount of 200 grams of poly(ethylene oxide)diamine was dissolved in a mixture of 74.4 grams deionized water and 74.4 grams 300 MW polyethylene glycol (PEG 300) and allowed to cool to room temperature. The resulting solution was charged into a one-liter glass container and placed in a water bath at room temperature with an overhead mechanical stirring paddle immersed in the solution. An amount of 16.68 grams of isophorone diisocyanate (IPDI) (available from Aldrich Chemical Company of Milwaukee, Wis.) was added portionwise over the course of several minutes, so as to maintain a temperature below 45° C. Stirring was continued for ten minutes until the solution became too viscous to satisfactorily stir. The mixing paddle was withdrawn and 6.96 grams of 2-vinyl-4,4-dimethyl-2-oxazolin-5-one (VDM) (available from S.N.P.E., of Princeton, N.J.) was added to the solution and mixed to obtain a homogeneous mixture, which was then capped and left in the dark overnight at room temperature.

The approximate molecular weight of the resulting chain extended, functionalized, poly(ethylene glycol) oligomeric precursor is 8000 and was calculated based on first principles with the assumption that the diamine and diisocyanate are of high purity and that the reactions go to completion with no side reactions. The resulting 60% percent solids solution was diluted to 30% solids with an equal amount of 1/1 PEG 300/water and 0.5% by weight of 2-hydroxy-1-[4-(hydroxyethoxy)phenyl]-2-methyl-1-propanone photoinitiator was added. The pH of the solution was measured at 8.5.

Examples 5A, 5B and Comparative Examples I, J were prepared by first dividing the solution into two equal parts. The first part was adjusted to a pH of 4.5 with acetic acid. This first part was then split into two more parts, representing Comparative Ex. I and Example 5A. Example 5A was then spiked with methacrylic acid to obtain a final concentration of 250 ppm. The second part of the original solution, which had a pH of 8.5 was then split into two more parts, representing Comparative Example J and Example 5B. Example 5B was also spiked with methacrylic acid to a final concentration of 250 ppm. Comparative Example J served as a control in that it was neither pH adjusted, nor spiked with methacrylic acid. Examples 5A, 5B and Comparative Examples I, J were UV cured in polyethylene foam wells that were 1.5 mm (60 mils) deep using a Fusion 300 system from Fusion UV Inc., equipped with a 118 W/cm (300 W/inch) H bulb. The total energy was maintained at 550 mJ/cm$^2$. The tack values after cure are shown in Table 7.

TABLE 7

| Example Number | pH of formulation | Methacrylic acid (ppm) | Tack |
|---|---|---|---|
| Comparative Ex. I | 4.5 | 0 | 2 |
| 5A | 4.5 | 250 | 6 |
| 5B | 8.5 | 250 | 2 |
| Comparative Ex. J | 8.5 | 0 | 2 |

While embodiments of the invention has been described, it will be appreciated that changes and modifications may be made to the various features of the embodiments described herein without departing from the spirit and scope of the invention.

What is claimed:

1. A process for preparing a pressure sensitive adhesive hydrogel, comprising:
    (A) providing an oligomeric precursor, the oligomeric precursor comprising a an alkylene oxide moiety endcapped with ethylenic unsaturation, the oligomeric precursor being associated with methacrylic acid, wherein the alkylene oxide moiety is of the formula:

—(—CH(R$^1$)—CH$_2$—O—)$_m$ . . . (—CH$_2$—CH$_2$—O—)$_n$— wherein the mole ratio of m:n is within a range of 1:9 to 9:1, and R$^1$ is a (C1-C4)alkyl group or H;
    (B) providing an ethylenically unsaturated crosslinking agent selected from the group consisting of difunctional ethylenically unsaturated monomer, trifunctional ethylenically unsaturated monomer and combinations of the foregoing; and
    (C) free radically curing the oligomeric precursor and the ethylenically unsaturated crosslinking agent in water in the presence of the methacrylic acid while controlling the pH to be between 3.5 and 9 during curing to provide the pressure sensitive adhesive hydrogel.

2. The process as defined in claim 1 wherein the alkylene oxide moiety is derived from a polymer selected from the group consisting of polyethylene glycol, poly[ethylene glycol co-propylene glycol] random copolymer and combinations of the foregoing.

3. The process as defined in claim 1 wherein ethylenic unsaturation is provided by reacting the polymer from which the alkylene oxide moiety is derived with methacrylic anhydride.

4. The process as defined in claim 1 wherein providing an oligomeric precursor in step (A) comprises reacting the polymer from which the alkylene oxide moiety is derived with methacrylic anhydride; and further comprising dissolving the oligomeric precursor in water to provide an oligomeric precursor solution.

5. The process as defined in claim 4 wherein the oligomeric precursor comprises polyethylene glycol dimethacrylate.

6. The process as defined in claim 4 wherein providing an oligomeric precursor in step (A) further comprises reacting the polymer from which the alkylene oxide moiety is derived with methacrylic anhydride in the presence of an oxygen scavenger to provide the alkylene oxide moiety endcapped with ethylenic unsaturation.

7. The process as defined in claim 6 wherein the oxygen scavenger is 2,6-di-tert-butyl-4-methylphenol.

8. The process as defined in claim 7 wherein the methacrylic acid is present in the reactive solution at a concentration greater than 100 ppm.

9. The process as defined in claim 1 wherein the oligomeric precursor has a weight average molecular weight of at least 6000.

10. The process as defined in claim 1 wherein the oligomeric precursor has a weight average molecular weight of at least 8000.

11. The process as defined in claim 1 wherein the oligomeric precursor has a weight average molecular weight of at least 12,000.

12. The process as defined in claim 1 wherein step (B) of providing an ethylenically unsaturated crosslinking agent comprises selecting the crosslinking agent from the group consisting of polyethylene glycol di(meth)acrylate, methylene bis (meth)acrylamide, ethoxylated bisphenol A di(meth)acrylate, alkanediol di(meth)acrylate, ethoxylated trimethylolpropane triacrylate, trimethylol propane tri(meth)acrylate, ethoxylated glyceryl tri(meth)acrylate, propoxylated glyceryltri(meth)acrylate, and combinations of two or more of the foregoing.

13. A process for preparing a pressure sensitive adhesive hydrogel, comprising:
    (A) providing an oligomeric precursor, the oligomeric precursor comprising an alkylene oxide moiety endcapped with ethylenic unsaturation, the oligomeric precursor being associated with methacrylic acid, wherein the alkylene oxide moiety is of the formula:

—(—CH(R$^1$)—CH$_2$—O—)$_m$ . . . (—CH$_2$—CH$_2$—O—)$_n$— wherein the mole ratio of m:n is within a range of 1:9 to 9:1, and R$^1$ is a (C1-C4)alkyl group;
    (B) providing an ethylenically unsaturated crosslinking agent selected from the group consisting of difunctional ethylenically unsaturated monomer, trifunctional ethylenically unsaturated monomer and combinations of the foregoing; and
    (C) free radically curing the oligomeric precursor and the ethylenically unsaturated crosslinking agent in water in the presence of the methacrylic acid while controlling the pH to be between 3.5 and 9 during curing to provide the pressure sensitive adhesive hydrogel; wherein free radically curing the oligomeric precursor and the ethylenically unsaturated crosslinking agent in step (C) is performed in the presence of a peroxide scavenger.

14. The process as defined in claim 13 wherein the peroxide scavenger is selected from the group consisting of thiodipropionic acid, fatty acid esters thereof and combinations of the foregoing.

15. The process as defined in claim 1 wherein free radically curing the oligomeric precursor and the ethylenically unsaturated crosslinking agent in step (C) comprises adding an initiator and exposing the oligomeric precursor and crosslinking agent to actinic radiation to initiate a polymerization reaction and provide the pressure sensitive adhesive hydro gel.

16. The process as defined in claim 1 wherein free radically curing the oligomeric precursor and the ethylenically unsaturated crosslinking agent in step (C) comprises adding an initiator and exposing the oligomeric precursor and crosslinking agent to ultraviolet radiation to initiate a polymerization reaction and provide the pressure sensitive adhesive hydrogel.

17. The process as defined in claim 1 wherein free radically curing the oligomeric precursor and the ethylenically unsaturated crosslinking agent in step (C) comprises adding an initiator material to initiate an oxidation/reduction reaction to initiate polymerization and provide the pressure sensitive adhesive hydrogel.

18. The process as defined in claim 1 wherein free radically curing the oligomeric precursor and the ethylenically unsaturated crosslinking agent in step (C) comprises dissolving the oligomeric precursor and the ethylenically unsaturated crosslinking agent in the same volume of water to provide a reactive solution; adding an ultraviolet initiator material to the reactive solution and exposing the reactive solution to ultraviolet radiation to initiate a polymerization reaction and provide the pressure sensitive adhesive hydrogel.

19. The process as defined in claim 1 wherein free radically curing the oligomeric precursor and the ethylenically unsaturated crosslinking agent in step (C) comprises dissolving the oligomeric precursor and the ethylenically unsaturated crosslinking agent in separate volumes of water to provide an oligomeric precursor solution and an ethylenically unsaturated monomer solution; combining the oligomeric precursor solution and the ethylenically unsaturated monomer solution to provide a reactive solution; adding an ultraviolet initiator material to the reactive solution and exposing the reactive solution to ultraviolet radiation to initiate a polymerization reaction and provide the pressure sensitive adhesive hydrogel.

20. The process as defined in claim 1 wherein the pressure sensitive adhesive hydrogel further comprises polar plasticizer selected from the group consisting of alcohols, mixtures of water and alcohol, glycerin, propylene glycol, dipropylene glycol, sorbitol, 1,3-butanediol, 1,4-butanediol, trimethylol propane, ethylene glycol and combinations of two or more of the foregoing.

21. The process as defined in claim 1 wherein the pressure sensitive adhesive hydrogel further comprises polar plasticizer comprising compounds represented by Formula I:

I wherein
M is hydrogen or $C_1$ through $C_6$ alkyl; and
m is an integer ranging from 1 to 25.

22. The process as defined in claim 1 wherein the pressure sensitive adhesive hydrogel further comprises polar plasticizer comprising polyethylene glycol.

23. The process as defined in claim 1 wherein free radically curing the oligomeric precursor and the ethylenically unsaturated crosslinking agent in step (C) is performed at a pH between 5 and 9.

24. The process as defined in claim 1 wherein free radically curing the oligomeric precursor and the ethylenically unsaturated crosslinking agent in step (C) is performed while controlling the pH to be between 6 and 8.

25. The process as defined in claim 1 further comprising (D) incorporating the pressure sensitive adhesive hydrogel into an article.

26. The process as defined in claim 25 wherein the article is a medical device.

27. The process as defined in claim 26 wherein the pressure sensitive adhesive hydrogel further comprises a salt and the medical device is a biomedical electrode.

28. The process as defined in claim 26 wherein the pressure sensitive adhesive hydrogel further comprises a pharmaceutical and the medical device is a pharmaceutical delivery device for delivering the pharmaceutical to or through mammalian skin.

29. The process as defined in claim 26 wherein the pressure sensitive adhesive hydrogel further comprises an antimicrobial agent and the medical device is a wound dressing.

30. A process for preparing a pressure sensitive adhesive hydrogel, comprising:
(A) providing an oligomeric precursor comprising a polyether dimethacrylate, the polyether dimethacrylate associated with methacrylic acid;
(B) providing an ethylenically unsaturated crosslinking agent selected from the group consisting of difunctional ethylenically unsaturated monomer, trifunctional ethylenically unsaturated monomer and combinations of the foregoing; and
(C) free radically curing the polyether dimethacrylate and the ethylenically unsaturated crosslinking agent in water in the presence of the methacrylic acid while controlling the pH to be between 3.5 and 9 during curing to provide the pressure sensitive adhesive hydrogel.

31. The process as defined in claim 30 wherein providing an oligomeric precursor in step (A) comprises reacting (a) polyether selected from the group consisting of polyethylene glycol, poly[ethylene glycol co-propylene glycol] random copolymer and combinations of the foregoing; with (b) methacrylic anhydride.

32. The process as defined in claim 31 wherein reacting (a) polyether with (b) methacrylic anhydride is accomplished in the presence of an oxygen scavenger.

33. The process as defined in claim 32 wherein the oxygen scavenger is 2,6-di-tert-butyl-4-methylphenol.

34. The process as defined in claim 33 further comprising dissolving the oligomeric precursor and methacrylic acid in water to provide an oligomeric precursor solution.

35. The process as defined in claim 30 wherein the oligomeric precursor has a weight average molecular weight of at least 6000.

36. The process as defined in claim 30 wherein the oligomeric precursor has a weight average molecular weight of at least 8000.

37. The process as defined in claim 30 wherein the oligomeric precursor has a weight average molecular weight of at least 12,000.

38. The process as defined in claim 30 wherein step (B) of providing an ethylenically unsaturated crosslinking agent comprises selecting the crosslinking agent from the group consisting of polyethylene glycol di(meth)acrylate, methylene bis (meth)acrylamide, ethoxylated bisphenol A di(meth)

acrylate, alkanediol di(meth)acrylate, ethoxylated trimethylolpropane triacrylate, trimethylol propane tri(meth)acrylate, ethoxylated glyceryl tri(meth)acrylate, propoxylated glyceryltri(meth)acrylate, and combinations of two or more of the foregoing.

39. A process for preparing a pressure sensitive adhesive hydrogel, comprising:
(A) providing an oligomeric precursor comprising a polyether dimethacrylate, the polyether dimethacrylate associated with methacrylic acid;
(B) providing an ethylenically unsaturated crosslinking agent selected from the group consisting of difunctional ethylenically unsaturated monomer, trifunctional ethylenically unsaturated monomer and combinations of the foregoing; and
(C) free radically curing the polyether dimethacrylate and the ethylenically unsaturated crosslinking agent in water in the presence of the methacrylic acid while controlling the pH to be between 3.5 and 9 during curing to provide the pressure sensitive adhesive hydrogel; wherein free radically curing the polyether dimethacrylate and the ethylenically unsaturated crosslinking agent in water in step (C) is performed in the presence of a peroxide scavenger.

40. The process as defined in claim 39 wherein the peroxide scavenger is selected from the group consisting of thiodipropionic acid, fatty acid esters thereof and combinations of the foregoing.

41. The process as defined in claim 30 wherein free radically curing the polyether dimethacrylate and the ethylenically unsaturated crosslinking agent in water in step (C) comprises adding an initiator and exposing the polyether dimethacrylate and the oligomeric precursor to actinic radiation to initiate a polymerization reaction and provide the pressure sensitive adhesive hydrogel.

42. The process as defined in claim 30 wherein free radically curing the polyether dimethacrylate and the ethylenically unsaturated crosslinking agent in water in step (C) comprises adding an initiator and exposing the polyether dimethacrylate and the oligomeric precursor to ultraviolet radiation to initiate a polymerization reaction and provide the pressure sensitive adhesive hydrogel.

43. The process as defined in claim 30 wherein free radically curing the polyether dimethacrylate and the ethylenically unsaturated crosslinking agent in water in step (C) comprises adding an initiator to initiate an oxidation/reduction reaction to initiate polymerization and provide the pressure sensitive adhesive hydrogel.

44. The process as defined in claim 30 wherein free radically curing the polyether dimethacrylate and the ethylenically unsaturated crosslinking agent in water in step (C) comprises dissolving the polyether dimethacrylate and the ethylenically unsaturated crosslinking agent in the same volume of water to provide a reactive solution; adding an ultraviolet initiator material to the reactive solution and exposing the reactive solution to ultraviolet radiation to initiate a polymerization reaction and provide the pressure sensitive adhesive hydro gel.

45. The process as defined in claim 30 wherein free radically curing the polyether dimethacrylate and the ethylenically unsaturated crosslinking agent in water in step (C) comprises dissolving the polyether dimethacrylate agent and the ethylenically unsaturated crosslinking agent in separate volumes of water to provide an oligomeric precursor solution and an ethylenically unsaturated monomer solution; combining the oligomeric precursor solution and the ethylenically unsaturated monomer solution to provide a reactive solution; adding an ultraviolet initiator material to the reactive solution and exposing the reactive solution to ultraviolet radiation to initiate a polymerization reaction and provide the pressure sensitive adhesive hydrogel.

46. The process as defined in claim 30 wherein the pressure sensitive adhesive hydrogel further comprises polar plasticizer selected from the group consisting of alcohols, mixtures of water and alcohol, glycerin, propylene glycol, dipropylene glycol, sorbitol, 1,3-butanediol, 1,4-butanediol, trimethylol propane, ethylene glycol and combinations of two or more of the foregoing.

47. The process as defined in claim 30 wherein the pressure sensitive adhesive hydrogel further comprises polar plasticizer comprising compounds represented by Formula I:

$$MO(CH_2CH_2O)_mH \qquad I$$

wherein
M is hydrogen or $C_1$ through $C_6$ alkyl; and
m is an integer ranging from 1 to 25.

48. The process as defined in claim 30 wherein the pressure sensitive adhesive hydrogel further comprises polar plasticizer comprising polyethylene glycol.

49. The process as defined in claim 30 wherein free radically curing the oligomeric precursor and the ethylenically unsaturated crosslinking agent in step (C) is performed while controlling the pH to be between about 5 and about 9.

50. The process as defined in claim 30 wherein free radically curing the oligomeric precursor and the ethylenically unsaturated crosslinking agent in step (C) is performed while controlling the pH to be between 6 and 8.

51. The process as defined in claim 30 further comprising (D) incorporating the pressure sensitive adhesive hydrogel into an article.

52. The process as defined in claim 51 wherein the article is a medical device.

53. The process as defined in claim 52 wherein the pressure sensitive adhesive hydrogel further comprises a salt and the medical device is a biomedical electrode.

54. The process as defined in claim 52 wherein the pressure sensitive adhesive hydrogel further comprises a pharmaceutical and the medical device is a pharmaceutical delivery device for delivering the pharmaceutical to or through mammalian skin.

55. The process as defined in claim 52 wherein the pressure sensitive adhesive hydrogel further comprises an antimicrobial agent and the medical device is a wound dressing.

56. The process of claim 1 further comprising combining the oligomeric precursor with a non-functionalized polymer to enhance the viscosity of the oligomeric precursor prior to free radically curing.

57. The process of claim 56 wherein the non-functionalized polymer is a poly(ethylene oxide), poly(acrylic acid), poly(N-vinyl pyrrolidone), poly(vinyl alcohol), or poly(acrylamide).

58. The process of claim 56 wherein the non-functionalized polymer is a hydrocolloid.

59. The process of claim 58 wherein the hydrocolloid comprises plant exudates, plant seed gums, seaweed extracts, cereal gums, fermentation or microbial gums, modified celluloses, pectin, gelatin, casein, or synthetic gums.

60. The process of claim 59 wherein the hydrocolloid comprises gum arabic, ghatti, karaya, tragacanth, guar, locust bean, acacia, agar, algin, alginate salts, carrageenin, starches, modified starches, dextran gum, xanthan gum, hydroxymethylcellulose, microcrystalline cellulose, carboxymethylcellulose, pectin, gelatin, casein, polyvinylpyrrolidone, low methoxyl pectin, propyleneglycol alginates, carboxymethyl locust bean gum, or carboxymethyl guar gum.

61. The process of claim 30 further comprising combining the oligomeric precursor with a non-functionalized polymer to enhance the viscosity of the oligomeric precursor prior to free radically curing.

62. The process of claim 30 wherein the non-functionalized polymer is a poly(ethylene oxide), poly(acrylic acid), poly(N-vinyl pyrrolidone), poly(vinyl alcohol), or poly(acrylamide).

63. The process of claim 30 wherein the non-functionalized polymer is a hydrocolloid.

64. The process of claim 63 wherein the hydrocolloid comprises plant exudates, plant seed gums, seaweed extracts, cereal gums, fermentation or microbial gums, modified celluloses, pectin, gelatin, casein, or synthetic gums.

65. The process of claim 64 wherein the hydrocolloid comprises gum arabic, ghatti, karaya, tragacanth, guar, locust bean, acacia, agar, algin, alginate salts, carrageenin, starches, modified starches, dextran gum, xanthan gum, hydroxymethylcellulose, microcrystalline cellulose, carboxymethylcellulose, pectin, gelatin, casein, polyvinylpyrrolidone, low methoxyl pectin, propyleneglycol alginates, carboxymethyl locust bean gum, or carboxymethyl guar gum.

66. A process for preparing a pressure sensitive adhesive hydrogel, comprising:
  (A) providing an oligomeric precursor, the oligomeric precursor comprising an ethylenically unsaturated-endcapped polyether, the oligomeric precursor being associated with methacrylic acid;
  (B) providing an ethylenically unsaturated crosslinking agent selected from the group consisting of difunctional ethylenically unsaturated monomer, trifunctional ethylenically unsaturated monomer and combinations of the foregoing; and
  (C) free radically curing the oligomeric precursor and the ethylenically unsaturated crosslinking agent in water in the presence of the methacrylic acid while controlling the pH to be between 3.5 and 9 during curing to provide the pressure sensitive adhesive hydrogel.

67. A process for preparing a pressure sensitive adhesive hydrogel, comprising:
  (A) providing an oligomeric precursor, the oligomeric precursor comprising a polyethylene glycol, poly[ethylene glycol co-propylene glycol] random copolymer, or combinations thereof, endcapped with ethylenic unsaturation, the oligomeric precursor being associated with methacrylic acid;
  (B) providing an ethylenically unsaturated crosslinking agent selected from the group consisting of difunctional ethylenically unsaturated monomer, trifunctional ethylenically unsaturated monomer and combinations of the foregoing; and
  (C) free radically curing the oligomeric precursor and the ethylenically unsaturated crosslinking agent in water in the presence of the methacrylic acid while controlling the pH to be between 3.5 and 9 during curing to provide the pressure sensitive adhesive hydrogel.

68. The process of claim 58 wherein the hydrocolloid is present in an amount of less than 5 wt-%, based on the total weight of the hydrogel.

* * * * *

UNITED STATES PATENT AND TRADEMARK OFFICE
CERTIFICATE OF CORRECTION

PATENT NO. : 7,999,023 B2
APPLICATION NO. : 11/004158
DATED : August 16, 2011
INVENTOR(S) : Vinod P Menon Page 1 of 1

It is certified that error appears in the above-identified patent and that said Letters Patent is hereby corrected as shown below:

Column 7
Line 67, Delete "intiators" and insert -- initiators --, therefor.

Column 13
Line 16, Delete "Maiden," and insert -- Malden, --, therefor.

Column 19
Line 7, Delete "Example 1," and insert -- Example I, --, therefor.
Line 44, In Claim 1, delete "a an" and insert -- an --, therefor.

Column 23
Line 58, In Claim 44, delete "hydro gel." and insert -- hydrogel. --, therefor.

Signed and Sealed this
Fourth Day of October, 2011

David J. Kappos
*Director of the United States Patent and Trademark Office*